United States Patent
Herron et al.

(10) Patent No.: US 9,874,551 B2
(45) Date of Patent: Jan. 23, 2018

(54) DETERMINING MINERALOGY OF AN EARTH FORMATION USING LINEAR REGRESSIONS

(71) Applicant: Schlumberger Technology Corporation, Sugar Land, TX (US)

(72) Inventors: Susan Herron, Cambridge, MA (US); Michael Herron, Cambridge, MA (US); Dale May, Bellville, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 723 days.

(21) Appl. No.: 14/211,751

(22) Filed: Mar. 14, 2014

(65) Prior Publication Data

US 2015/0260034 A1    Sep. 17, 2015

(51) Int. Cl.
*G01N 33/24* (2006.01)
*G01V 5/10* (2006.01)
*E21B 49/00* (2006.01)

(52) U.S. Cl.
CPC .............. *G01N 33/24* (2013.01); *G01V 5/10* (2013.01); *E21B 49/00* (2013.01)

(58) Field of Classification Search
CPC . G01N 33/24; G01V 5/04; G01V 5/10; G01V 5/107; E21B 49/00
USPC .......................................................... 702/11
See application file for complete search history.

(56) References Cited

U.S. PATENT DOCUMENTS

| 8,217,337 B2 * | 7/2012 | Neville | G01V 5/04 250/254 |
| 2007/0246649 A1 | 10/2007 | Jacobi et al. | |
| 2013/0046469 A1 * | 2/2013 | Herron | G01N 21/3563 702/2 |
| 2014/0214324 A1 * | 7/2014 | Freedman | G01V 5/08 702/8 |

OTHER PUBLICATIONS

U.S. Appl. No. 13/791,931, filed Mar. 9, 2013.

* cited by examiner

*Primary Examiner* — Bryan Bui
(74) *Attorney, Agent, or Firm* — Michael Dae

(57) ABSTRACT

A method for determining mineralogy of a formation includes determining a model of arenites in the formation by performing a first type of linear regression on a plurality of elemental dry weights of the formation based upon a sum of elemental dry weights of calcium and magnesium being at least a given value, or performing a second type of linear regression on the elemental dry weights based upon the sum of the elemental dry weights of elemental calcium and magnesium being less than the given value. A model of arkoses in the formation is determined by performing a third type of linear regression on the elemental dry weights. A partitioning function is then determined. The mineralogy of the formation is then determined by applying the partitioning function to the model of arenites and the model of arkoses, and adding the model of arenites and the model of arkoses together.

18 Claims, 5 Drawing Sheets

DETERMINING MINERALOGY OF AN EARTH FORMATION USING LINEAR REGRESSIONS

BACKGROUND

Modern suites of well logging measurements are used to predict porosity and fluid saturations of reservoir rocks surrounding a borehole. Porosity and fluid saturations are useful for accurate reserve estimation and identification of potential hydrocarbon bearing zones. More accurate porosities and fluid saturations may be predicted if detailed and accurate mineralogical information is available. Mineralogical data provide more accurate characterization of logging tool responses and, as a result, lead to improved log interpretations. Knowledge of the clay mineral types present in reservoir rocks and their volumes is an indicator of reservoir quality and is also used in the selection of hydraulic fracturing, completion, and stimulation fluids.

Elemental spectroscopy logging tools provide elemental compositions of reservoir rocks (e.g., Si, Al, Ca, Mg, K, Fe, S, etc.) derived from capture and inelastic neutron gamma ray spectroscopy. The elemental compositions are given as the weight fractions of the individual elements present in the rock matrix. They are used to predict mineralogy and rock properties such as grain density. The inversion of elemental composition to predict accurate mineralogy is a complex issue in reservoir characterization. The complexity arises because of the large number of minerals that are commonly found in reservoir rocks and the variability of the compositions of these minerals. Moreover, the mineralogy inversion problem may be complicated by the fact that many of the measured elements are common to different minerals. Thus, there exists a degree of non-uniqueness in the reconstruction of mineralogy from elemental composition data.

Because of the complexity of the mathematical relationship between elemental composition and mineralogy it is difficult to derive accurate forward models that predict mineralogy from rock chemistry. This is also true for most other reservoir characterization issues for which idealized forward models do not accurately account for the behavior of complex reservoir rocks and fluids.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A method is for determining mineralogy of an earth formation. The method may include determining a model of arenites in the earth formation by using a processor to perform a first type of linear regression on a plurality of elemental dry weights of the earth formation based upon a sum of elemental dry weights of calcium and magnesium being at least a given value, or perform a second type of linear regression on the plurality of elemental dry weights based upon the sum of the elemental dry weights of elemental calcium and magnesium being less than the given value. The method may also include determining a model of arkoses in the earth formation, by performing a third type of linear regression on the plurality of elemental dry weights, using the processor, as well as determining a partitioning function, using the processor. The mineralogy of the earth formation may be determined by using the processor to apply the partitioning function to the model of arenites and the model of arkoses, and add the model of arenites and the model of arkoses together.

Another aspect is directed to a method for determining mineralogy of an earth formation. This method may include determining a model of arenites in the earth formation, by performing at least one type of linear regression on a plurality of elemental dry weights of the earth formation, using a processor. A model of arkoses in the earth formation may be determined by performing another type of linear regression on the plurality of elemental dry weights, using the processor. A partitioning function may be determined, using the processor. The method may further include determining the mineralogy of the earth formation by using the processor to apply the partitioning function to the model of arenites and the model of arkoses, and add the model of arenites and the model of arkoses together.

A device aspect is directed to an apparatus for determining mineralogy of an earth formation. The apparatus may include a downhole tool for obtaining information about the earth formation, and a processor associated with the downhole tool. The processor may be for determining a plurality of elemental dry weights of the earth formation based upon the information obtained by the downhole tool, and for determining a model of arenites in the earth formation. The processor may determine the model of arenites by performing a first type of linear regression on a plurality of elemental dry weights of the earth formation based upon a sum of elemental dry weights of calcium and magnesium being at least a given value, or perform a second type of linear regression on the plurality of elemental dry weights based upon the sum of the elemental dry weights of elemental calcium and magnesium being less than the given value. The processor may also be for determining a model of arkoses in the earth formation, by performing a third type of linear regression on the plurality of elemental dry weights, and for determining a partitioning function. The processor may also determine the mineralogy of the earth formation by applying the partitioning function to the model of arenites and the model of arkoses, and adding the model of arenites and the model of arkoses together.

DETAILED DESCRIPTION

The present description is made with reference to the accompanying drawings, in which example embodiments are shown. However, many different embodiments may be used, and thus the description should not be construed as limited to the embodiments set forth herein. Rather, these embodiments are provided so that this disclosure will be thorough and complete. Like numbers refer to like elements throughout.

In order to determine the mineralogy of an earth formation without using core samples, it is helpful to determine the dry weight of elements at a variety of locations of varying depth in the formation (i.e. the dry weight of elements every X inches in the formation is determined). This can be done using gamma ray spectroscopy. For example, as will be understood by those of skill in the art, a nuclear tool containing a neutron source such as generator or chemical source and one or more gamma ray detectors can be lowered into a borehole in the earth formation, the neutron source used to irradiate the formation with neutrons, and the detectors monitored for gamma rays resulting from neutron capture events in the formation and/or inelastic scattering of the neutrons off atoms of the formation. As also understood by those of skill in the art, data obtained from the gamma ray detectors may be processed so as to obtain raw concentrations of elements in the formation, which may then be further processed to obtain the elemental dry weights which are useful for determining mineralogy. Rather than using gamma ray spectroscopy, other techniques (such as x-ray fluorescence, inductively coupled plasma atomic emission spectroscopy, inductively coupled plasma mass spectrometry, instrumental neutron activation analysis, etc) may be used to determine the dry weights of the elements, and the resulting data may be processed to obtain the elemental dry weights.

Figure 1:
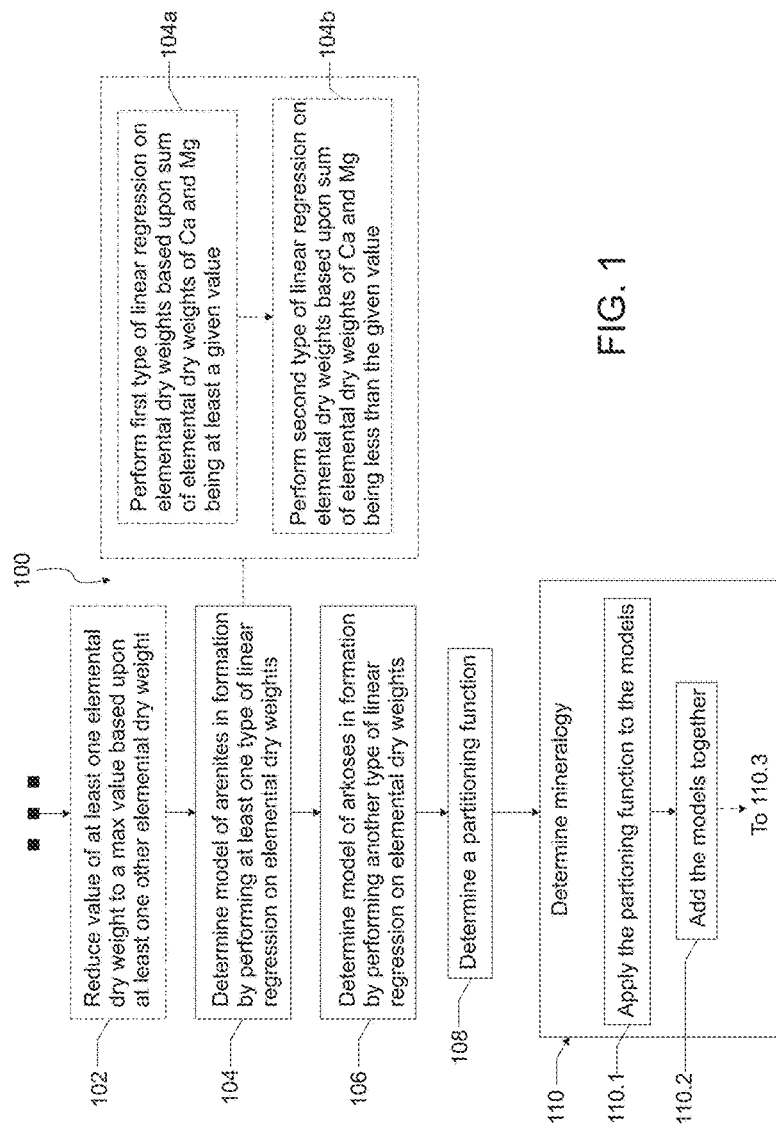
FIG. 1 shows a method of determining mineralogy of rock, such as an earth formation, in accordance with the present disclosure.

Referring initially to the flowchart 100 of FIG. 1, a method for determining the mineralogy of an earth formation is now described. Initially, if helpful given the values of the elemental dry weights, a value of at least one of the elemental dry weights is reduced to a corresponding maximum value for that elemental dry weight, based upon at least one other elemental dry weight (Block 102). This is done for multiple reasons. The determination of certain elemental dry weights, such as Aluminum and Potassium, may have a higher degree of uncertainty than the determination of other elemental dry weights, for example caused by the difference in the cross section of the neutron-gamma ray reactions of different elements used in gamma ray spectroscopy, and/or caused by cross-talk between different elements in the acquired gamma ray spectrum. When performing linear regressions used in this method for determining mineralogy, which will be explained in detail below, certain elemental dry weights may have values that might reflect statistical uncertainties rather than actual concentrations of elements, such as potassium or aluminum in a carbonate environment, could lead to erroneous or inaccurate mineralogy results. For example, elemental dry weights of potassium above a threshold point can result in a determination that the mineralogy in a given zone of the formation includes small amounts of clays and feldspars, when in actuality the mineralogy of the rock in the given zone is close to a pure carbonate. Therefore, to mitigate the effects caused by the elemental dry weight of potassium being above the threshold, it is useful to reduce the value of the elemental dry weight of potassium based upon the elemental dry weight of aluminum. That is, for a given value of the elemental dry weight of aluminum in a zone of the formation, the value of the elemental dry weight of potassium in that zone is limited to a maximum. Thus, if the elemental dry weight of potassium was originally above the maximum, it is reduced to the maximum, whereas if the elemental dry weight of potassium was not originally above the maximum, the value remains unchanged.

Next, a model of arenites in the earth formation is determined (Block 104). The arenite model can be either a carbonate arenite model or a siliciclastic arenite model, depending upon which linear regression is used. The model of the arenites is determined by performing a first type of linear regression (such as a carbonate arenite linear regression) on selected elemental dry weights of the earth formation (the dry weights used for this linear regression may or may not include all the dry weights determined using gamma ray spectroscopy), if the sum of the elemental dry weights of certain elements, such as calcium and magnesium, is greater than or equal to a given value, such as the carbonate point (Block 104a). On the other hand, if the sum of the elemental dry weights of these certain elements (i.e. calcium and magnesium) is less than the given value (i.e. the carbonate point), a second type of linear regression (such as a siliciclastic arenite linear regression) is performed on the selected elemental dry weights of the earth formation (Block 104b). Thus, as should be apparent, the type of linear regression used to determine the model of arenites may depend upon the amount of carbonates present in the earth formation.

The model of arenites includes a dry weight of certain minerals in the earth formation. A separate linear regression is performed for each of the mineral dry weights to be determined. The linear regression for each mineral dry weight may take the form of:

dry weight mineral 1=offset+a*(element 1)+b*(element 2)+c*(element 3)+d*(element 4)+e*(element 5)+f*(element 6)+g*(element 7).

with a, b, c, d, e, f, and g denoting constants that may be positive or negative. When it is said that different types of linear regressions are performed, it is meant that different elements may be included in each type of linear regression, and that different constants may be used for elements common to each type of linear regression. The linear regressions used herein may be derived from a database of mineralogy and chemistry. Coefficients for such linear regressions may be determined by solving using an optimization technique such as multiple linear regression. For example, it is possible to solve for the coefficients a, b, and c in the equation:

$$\text{dry weight quartz} = a*Si + b*Fe + c*Ca$$

This solution can contain an offset, and it can contain any selected set of elements.

After determining the models of arenites, a model of arkoses in the earth formation is determined by performing a third type of linear regression (different from the first and second types of linear regressions) on the selected elemental dry weights (Block 106).

Then, a partitioning function is determined (Block 108), and applied to the arenite and arkose models to weight them (Block 110.1). The weighted arenite and arkose models are then added together to create a combined model (Block 110.2). This partitioning function may be based on a priori knowledge, such as that gained from analysis of a core sample, analysis of other measurements of formation properties, or past mineralogy determinations. The partitioning function may additionally or alternatively be based upon one or more elemental dry weights, for example the elemental dry weighs of potassium and sodium.

When basing the partitioning function on one or more elemental dry weights, it may be useful to average the elemental dry weights over multiple depth levels. For example, the gamma ray spectroscopy may be performed every 6 in such that elemental dry weights are calculated for every 6 in of depth. Therefore, it may be useful to average the elemental dry weights over an 18 in interval, for example, which may represent the elemental dry weights at the depth level before the level for which the partitioning function is being calculated, at the depth level for which the partitioning function is being calculated, and at the depth level after the depth level for which the partitioning function is being calculated. Intervals of any suitable number of depths may be used, and interval may start with, end with, or contain the depth level for which the partitioning function is being calculated.

Figures 3A, 3B:
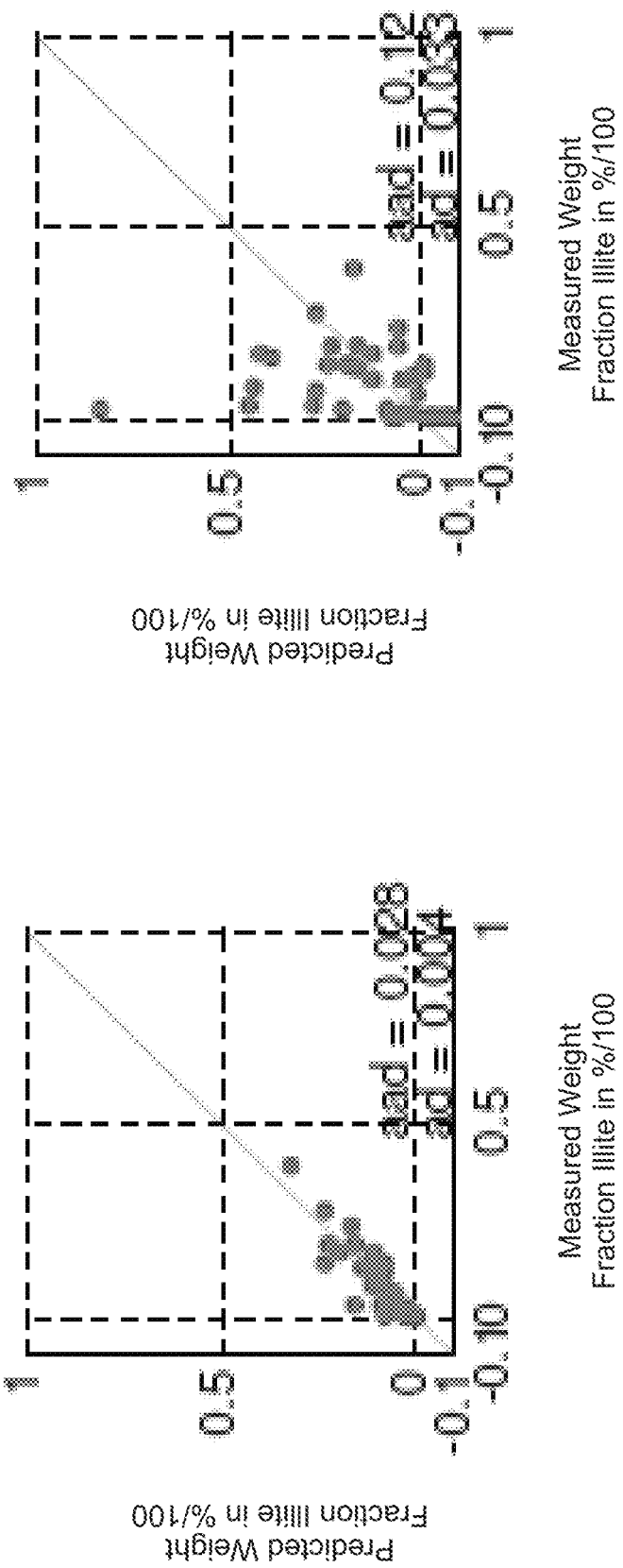
FIG. 3A shows predicted vs. actual values of illite as determined by using the arenite regression.
FIG. 3B shows predicted vs. actual values of illite as determined by using the arkose regression.
Figure 4A:
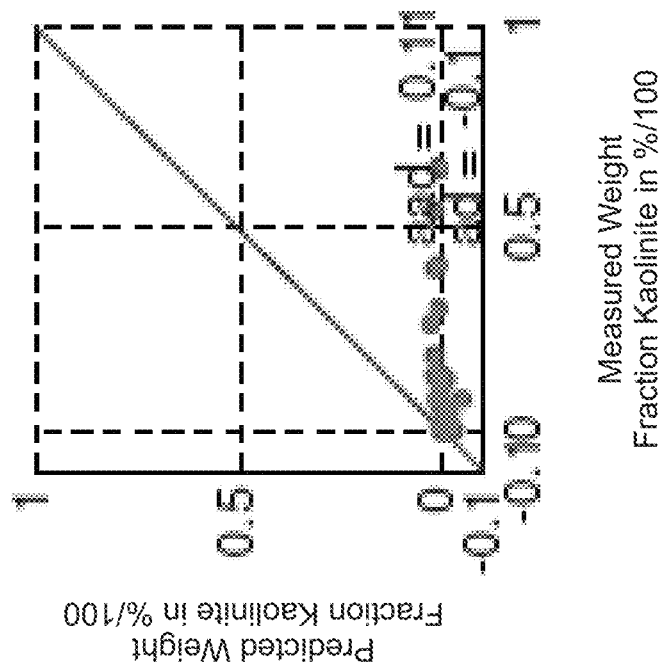
FIG. 4A shows predicted vs. actual values of kaolinite as determined by using the arenite regression.
Figure 4B:
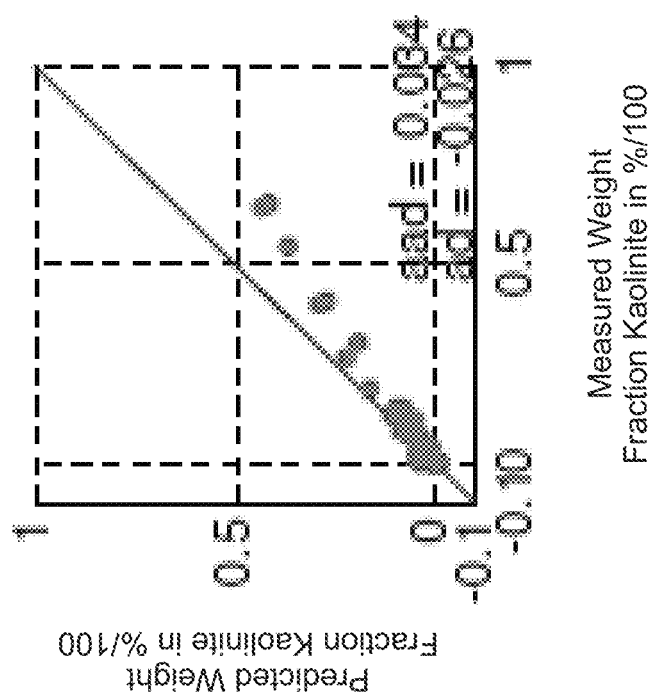
FIG. 4B shows predicted vs. actual values of kaolinite as determined by using the arkose regression.

The purpose for separate arenite and arkose regressions is that depending on whether the rock tends to be arenite or arkose in nature, one regression may yield more accurate results than another. For example, as shown in FIG. 3A, the predicted vs. actual (as verified using laboratory analysis techniques or other logging techniques, for example) values of illite when the arenite regression is performed match up well, whereas, as shown in FIG. 3B, the predicted vs. actual values of illite when the arkose regression is performed don't match up as well. This is due to the fact that the samples come from an arenite (low feldspar content) formation rather than an arkose formation, so the regression is applicable. As another example, for a different sample, shown in FIGS. 4A and 4B are values for kaolinite when arenite (4A) and arkose (4B) regressions are performed. Again, the arenite regression produces a better fit than the arkose regression, because the sample comes from an arenite type rock.

Figure 2:
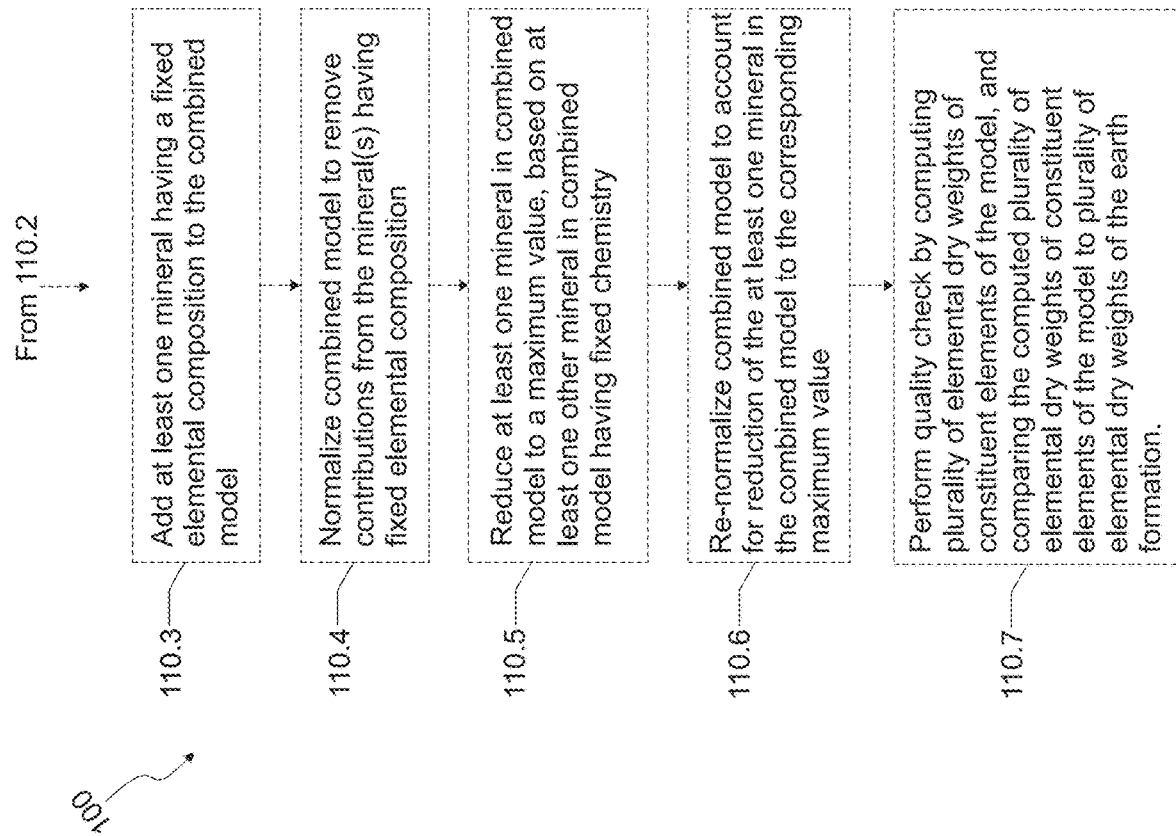
FIG. 2 shows optional further steps of the method of FIG. 1.

Next, as shown in the flowchart of FIG. 2, at least one mineral having a fixed elemental composition is added to the combined model (Block 110.3). By fixed elemental composition, it is meant that the chemical formulae for such minerals remain constant. Examples of such fixed elemental composition minerals include pyrite, anhydrite, and salt. The concentrations of these fixed elemental composition minerals in the earth formation may be determined separately than the other minerals (i.e. determined by methods other than the arenite and arkose linear regressions discussed above). Since the concentrations in the determined mineralogy add up to one (i.e. 100%, and thus the total mineralogy of the earth formation), and since the concentrations of these fixed elemental composition minerals are determined separately, it is useful to normalize the combined model to remove contributions from the minerals having the fixed elemental composition (Block 110.4). In some applications, certain minerals without fixed elemental compositions, such as coal, may also be determined separately, and the same sort of normalization as described above may be performed for these certain minerals as well.

Next, if helpful based upon minerals in the combined model, at least one mineral in the combined model is reduced to a maximum value based on one or more other minerals in the combined model that have a fixed elemental composition (Block 110.5). Examples of such fixed elemental composition minerals, based upon which minerals in the combined models are reduced to maximum values, include quartz, calcite, dolomite, and siderite. This reduction is done to help ensure the determined mineralogy does not give values of certain minerals inconsistent with the actual composition of those materials. For example, the elemental dry weight of silicon in pure quartz is 0.467 (i.e. 46.7%), and therefore it would not be desirable for the determined mineralogy to indicate an amount of quartz present that is greater than the elemental dry weight of silicon divided by 0.467.

Thereafter, the combined model is re-normalized to account for the reduction of the one or more minerals to their maximum values (Block 110.6). At this point, the mineralogy of the earth formation can be considered to be determined. The mineralogy may include quartz, and/or albite, and/or anorthite, and/or orthoclase, and/or kaolinite, and/or illite, and/or smectite, and/or chlorite, and/or muscovite, and/or biotite, and/or calcite, and/or dolomite, and/or siderite, and/or ankerite, and/or pyrite, and/or anhydrite, and/or salt, and/or coal.

A quality check may then be performed on the model by computing the elemental dry weights of constituent minerals of the model, and comparing these computed elemental dry weights to the elemental dry weights of the earth formation that were determined via gamma ray spectroscopy (Block 110.7). Depending on the degree of match, it may be known that the model is sufficiently accurate, or that the model could be manually adjusted by a log analyst to be sufficiently accurate, or that the model is not sufficiently accurate. Causes for the model not being sufficiently accurate can include errors with the tool that was used to determine the elemental dry weights of the earth formation using gamma ray spectroscopy, where a priori knowledge was improperly relied upon to determine the weighting function, where minerals are present in the earth formation that were not included in the model, etc.

Figure 5:
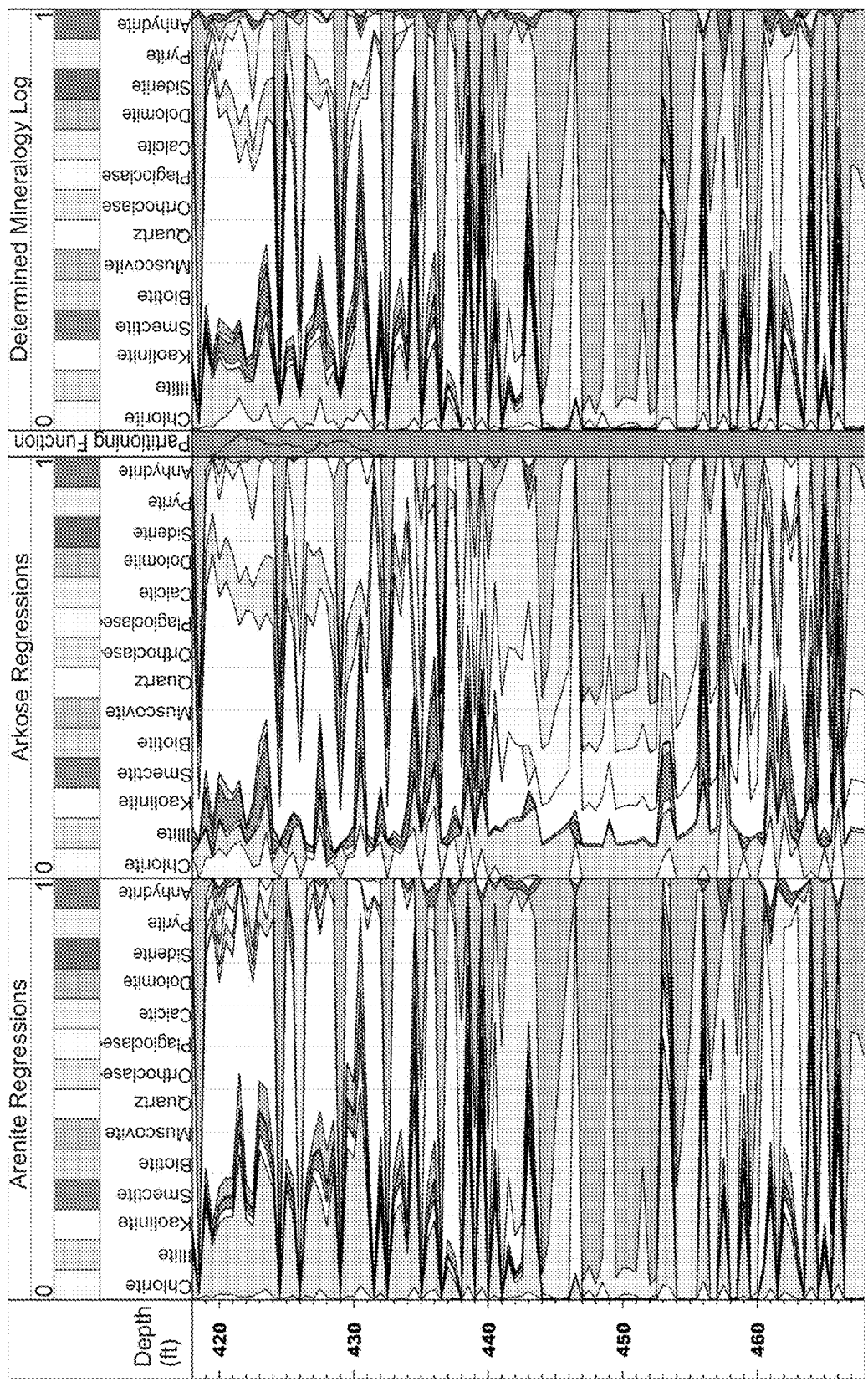
FIG. 5 shows sample results of the arenite and arkose regressions, the partitioning function used to combine the arenite and arkose regressions, and the determined mineralogy log.

Sample logs of a test subsurface formation are shown in FIG. 5. Here, separate logs are shown for each mineral determined, using both the arenite and arkose regressions. The partitioning function and the determined mineralogy log are shown as well. When viewed side by side, the differences in results between the arenite and arkose regressions become apparent. For example, the arkose regression shows a greater amount of chlorite than the arenite regression and the arenite regression shows a greater amount of illite than the arkose regression. In addition, the application of the partitioning function in combining the regressions is apparent by viewing the regressions together with the determined mineralogy log.

While the disclosure has been described with respect to a given number of embodiments, those skilled in the art, having benefit of this disclosure, will appreciate that other embodiments may be implemented that do not depart from the scope of the disclosure as disclosed herein. Many modifications and other embodiments will come to the mind of one skilled in the art having the benefit of the teachings presented in the foregoing descriptions and the associated drawings. Therefore, it is understood that various modifications and embodiments are intended to be included within the scope of the appended claims.

The invention claimed is:

1. A method for determining mineralogy of rock comprising:
lowering an elemental spectroscopy logging tool into a borehole penetrating the rock;
irradiating the rock with neutrons emitted by the elemental spectroscopy logging tool;
measuring gamma rays from the rock resulted from said irradiating;
determining a model of arenites in the rock by using a processor to
perform a first type of linear regression on a plurality of elemental dry weights of the rock based upon a sum of elemental dry weights of calcium and magnesium being at least a given value, or perform a second type of linear regression on the plurality of elemental dry weights based upon the sum of the elemental dry weights of elemental calcium and magnesium being less than the given value;

determining a model of arkoses in the rock, by performing a third type of linear regression on the plurality of elemental dry weights, using the processor;

determining a partitioning function, using the processor; and determining the mineralogy of the rock by using the processor to apply the partitioning function to the model of arenites and the model of arkoses, and add the model of arenites and the model of arkoses together to create a combined model;

using the determined mineralogy of the rock in a drilling, simulation, or completion, operation on the wellbore penetrating the rock.

2. The method of claim 1, wherein the given value is a carbonate point.

3. The method of claim 1, wherein the sum of the elemental dry weights of calcium and magnesium being less than the given value indicates an amount of carbonates in the rock being less than an amount of carbonates in the rock if the sum of the calcium and magnesium elemental dry weights had been at least the given value.

4. The method of claim 1, wherein the partitioning function is based upon at least one elemental dry weight and/or a priori knowledge.

5. The method of claim 1, wherein the partitioning function is based upon elemental dry weights of potassium and/or sodium.

6. The method of claim 1, wherein the models of arenites and arkoses are determined at a plurality of depth levels in the rock.

7. The method of claim 6, wherein the partitioning function used for the models of arenites and arkoses at a given depth level is based upon averages of potassium and/or sodium elemental dry weights over at least some of the plurality of depth levels.

8. The method of claim 6, wherein the partitioning function used for the models of arenites and arkoses at a given depth level is based upon averages of potassium and/or sodium elemental dry weights over an interval of the plurality of depth levels containing the given depth level.

9. The method of claim 1, wherein the determined mineralogy of the rock includes at least one of the group consisting of quartz, albite, anorthite, orthoclase, kaolinite, illite, smectite, chlorite, muscovite, biotite, calcite, dolomite, siderite, ankerite, pyrite, anhydrite, salt, and coal.

10. The method of claim 1, further comprising reducing a value of at least one elemental dry weight to a corresponding maximum value, based upon at least one other elemental dry weight, prior to performing the first type of linear regression.

11. The method of claim 1, further comprising reducing a value of at least one mineral in the determined mineralogy of the rock to a corresponding maximum value, based upon at least one elemental dry weight.

12. The method of claim 1, further comprising reducing a value of an elemental dry weight of potassium to a maximum potassium value, based upon an elemental dry weight of aluminum, prior to performing the first type of linear regression.

13. The method of claim 1, further comprising adding at least one mineral having a fixed elemental composition to the combined model; and further comprising normalizing the combined model such that a sum of concentrations of the at least one mineral having the fixed elemental composition and concentrations of minerals in the determined model is 100%.

14. The method of claim 13, wherein the at least one mineral having a fixed elemental composition includes at least one of the group consisting of pyrite, anhydrite, coal, and salt.

15. The method of claim 13, further comprising reducing at least one mineral in the combined model to a corresponding maximum value, based upon at least one other mineral in the combined model having a fixed elemental composition.

16. The method of claim 15, wherein the at least one other mineral having a fixed elemental composition includes at least one of the group consisting of quartz, calcite, dolomite, and siderite.

17. The method of claim 15, further comprising re-normalizing the combined model to account for the reduction of the at least one mineral in the combined model to the corresponding maximum value.

18. The method of claim 17, further comprising performing a quality check by computing a plurality of elemental dry weights of constituent elements of the model, and comparing the computed plurality of elemental dry weights of constituent elements of the model to the plurality of elemental dry weights of the rock.

* * * * *